(12) United States Patent
Williamson et al.

(10) Patent No.: US 11,143,644 B2
(45) Date of Patent: Oct. 12, 2021

(54) SYSTEM AND METHOD FOR DETERMINING A CONTAMINATION LEVEL IN AN EMISSIONS MEASUREMENT DEVICE OR SYSTEM

(71) Applicant: AVL TEST SYSTEMS, INC., Plymouth, MI (US)

(72) Inventors: James Patrick Williamson, Dexter, MI (US); Benjamin C. Shade, Whitmore Lake, MI (US)

(73) Assignee: AVL TEST SYSTEMS, INC., Plymouth, MI (US)

( * ) Notice: Subject to any disclaimer, the term of this patent is extended or adjusted under 35 U.S.C. 154(b) by 105 days.

(21) Appl. No.: 16/443,060

(22) Filed: Jun. 17, 2019

(65) Prior Publication Data

US 2019/0391121 A1      Dec. 26, 2019

Related U.S. Application Data

(60) Provisional application No. 62/688,692, filed on Jun. 22, 2018.

(51) Int. Cl.
*G01M 15/10* (2006.01)
*G01N 33/00* (2006.01)
(Continued)

(52) U.S. Cl.
CPC ............. *G01N 33/007* (2013.01); *G01N 1/38* (2013.01); *G01N 15/06* (2013.01);
(Continued)

(58) Field of Classification Search
CPC .... G01N 33/007; G01N 33/0018; G01N 1/38; G01N 1/2252; G01N 1/2258;
(Continued)

(56) References Cited

U.S. PATENT DOCUMENTS 6,387,706 B1 * 5/2002 Eden .................. G01N 33/0011
  436/127
6,470,732 B1 * 10/2002 Breton .................. F01N 13/008
  73/114.69

(Continued)

FOREIGN PATENT DOCUMENTS

JP           3992121 B2 * 10/2007

OTHER PUBLICATIONS

AIAA 94-01 18, Emissions Predictions of Different Gas Turbine Combustors, N. K. Rizk and H. C. Mongia Allison Engine Company, Inc. Indianapolis (Year: 1994).*

(Continued)

*Primary Examiner* — Herbert K Roberts
*Assistant Examiner* — Fatemeh Esfandiari Nia
(74) *Attorney, Agent, or Firm* — Honigman LLP; Matthew H. Szalach (57) ABSTRACT

An emissions test system includes an emissions analyzer, a contamination index module, and a diagnostic module. The emissions analyzer is configured to determine a concentration of an emission in a sample of exhaust gas from an engine. The contamination index module is configured to determine a contamination index based on at least two of a flow rate of the exhaust gas sample, the concentration of the emission in the exhaust gas sample, an operating duration of the emissions test system, a pressure of the exhaust gas, and a temperature of the exhaust gas. The diagnostic module is configured to identify potential contamination of at least one of the emissions test system and a component in the emissions test system based on the contamination index.

20 Claims, 4 Drawing Sheets

(51) Int. Cl.
*G01N 1/38* (2006.01)
*G01N 15/06* (2006.01)

(52) U.S. Cl.
CPC ....... *G01N 33/0018* (2013.01); *G01M 15/102* (2013.01); *G01N 33/0016* (2013.01)

(58) Field of Classification Search
CPC ........ G01N 2001/2255; G01M 15/102; G01M 15/106; G01M 15/048
See application file for complete search history.

(56) References Cited

U.S. PATENT DOCUMENTS

| | | |
|---|---|---|
| 9,116,138 B2 * | 8/2015 | Okada ................. G01M 15/102 |
| 2012/0090382 A1 * | 4/2012 | Favre ................. G01N 33/0018 73/31.06 |
| 2013/0118244 A1 * | 5/2013 | Okada ................ G01N 33/0063 73/114.71 |
| 2013/0136656 A1 | 5/2013 | Okada et al. |
| 2013/0312487 A1 | 11/2013 | Miyai et al. |
| 2018/0164184 A1 * | 6/2018 | Kumagai ................. G01F 1/46 |

OTHER PUBLICATIONS

Translation of Search Report dated May 14, 2020 corresponding to German Patent Application No. 10 2019 116 831.7, 5 pages.

* cited by examiner

SYSTEM AND METHOD FOR DETERMINING A CONTAMINATION LEVEL IN AN EMISSIONS MEASUREMENT DEVICE OR SYSTEM

CROSS-REFERENCE TO RELATED APPLICATIONS

This application claims the benefit of U.S. Provisional Application No. 62/688,692, filed on Jun. 22, 2018. The entire disclosure of the application referenced above is incorporated herein by reference.

FIELD

The present disclosure relates to emissions test systems, and more particularly, to systems and methods for determining a contamination level in an emissions measurement device or system.

BACKGROUND

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Emissions test systems collect exhaust gas produced by an engine and measure the concentrations of emissions in the exhaust gas. The concentration of an emission measured during a period is multiplied by the mass flow rate of exhaust gas during that period to obtain the mass flow rate of the emission. The mass flow rate of the emission is then multiplied by the duration of the period to obtain the total mass of the emission in the exhaust gas produced by the engine during the period.

A constant volume sampling (CVS) system is a type of emissions test system that enables determining the mass of emissions in exhaust gas without measuring the flow rate of the exhaust gas, which simplifies emission mass determinations. A CVS system typically includes a dilution tunnel in which exhaust gas and a dilution gas are mixed, a sample probe that directs a sample of the diluted exhaust gas from the dilution tunnel to a sample collector, and a blower disposed downstream of the dilution tunnel. The blower draws a constant volume of diluted exhaust gas through the dilution tunnel. Thus, the exhaust gas flow rate may be determined by subtracting the flow rate of the dilution gas from the flow rate of the diluted exhaust gas.

SUMMARY

An emissions test system according to the present disclosure includes an emissions analyzer, a contamination index module, and a diagnostic module. The emissions analyzer is configured to determine a concentration of an emission in a sample of exhaust gas from an engine. The contamination index module is configured to determine a contamination index based on at least two of a flow rate of the exhaust gas sample, the concentration of the emission in the exhaust gas sample, an operating duration of the emissions test system, a pressure of the exhaust gas, and a temperature of the exhaust gas. The diagnostic module is configured to identify potential contamination of at least one of the emissions test system and a component in the emissions test system based on the contamination index In one example, the emissions test system further includes a dilution tunnel and a sample collector. The dilution tunnel is configured to receive the exhaust gas from the engine and dilution gas from a dilution gas source. The sample collector is configured to receive a sample of diluted exhaust gas from the dilution tunnel. The emissions analyzer is configured to determine the concentration of the emission in the diluted exhaust gas sample.

In one example, the exhaust gas sample is undiluted.

In one example, the contamination index module is configured to determine the contamination index based on the sample flow rate and the emission concentration.

In one example, the contamination index module is configured to determine the contamination index based on at least three of the sample flow rate, the emission concentration, the system operating duration, the exhaust pressure, and the exhaust temperature.

In one example, the contamination index module is configured to determine the contamination index based on the sample flow rate, the emission concentration, the system operating duration, the exhaust pressure, and the exhaust temperature.

In one example, the contamination index module is configured to determine the contamination index based on (i) a first product of a first weighting factor and a first one of the sample flow rate, the emission concentration, the system operating duration, the exhaust pressure, and the exhaust temperature, and (ii) a second product of a second weighting factor and a second one of the sample flow rate, the emission concentration, the system operating duration, the exhaust pressure, and the exhaust temperature, the second weighting factor having a different value than the first weighting factor.

In one example, the contamination index module is configured to determine the contamination index based on (i) a first result of a first one of the sample flow rate, the emission concentration, the system operating duration, the exhaust pressure, and the exhaust temperature raised to the power of a first exponent, and (ii) a second result of a second one of the sample flow rate, the emission concentration, the system operating duration, the exhaust pressure, and the exhaust temperature raised to the power of a second exponent, the second exponent having a different value than the first exponent.

In one example, the contamination index module is configured to determine the contamination index at regular intervals to yield a plurality of contamination index values, and identify potential contamination of at least one of the emissions test system and the emissions test system component when a sum of the contamination index values is greater than a predetermined value.

In one example, the contamination index module is configured to recommend that a user perform maintenance on the emissions test system when the sum of the contamination index values is greater than the predetermined value, and set the sum of the contamination index values to zero when the user indicates that the maintenance has been performed.

A method according to the present disclosure includes determining a contamination index based on at least two of a flow rate of an exhaust gas sample passing through an emissions test system, a concentration of an emission in the exhaust gas sample, an operating duration of the emissions test system, a pressure of the exhaust gas, and a temperature of the exhaust gas, and identifying potential contamination of at least one of the emissions test system and a component in the emissions test system based on the contamination index.

In one example, the exhaust gas sample is diluted with a dilution gas.

In one example, the exhaust gas sample is undiluted.

In one example, the method further includes determining the contamination index based on the sample flow rate and the emission concentration.

In one example, the method further includes determining the contamination index based on at least three of the sample flow rate, the emission concentration, the system operating duration, the exhaust pressure, and the exhaust temperature.

In one example, the method further includes determining the contamination index based on the sample flow rate, the emission concentration, the system operating duration, the exhaust pressure, and the exhaust temperature.

In one example, the method further includes determining the contamination index based on (i) a first product of a first weighting factor and a first one of the sample flow rate, the emission concentration, the system operating duration, the exhaust pressure, and the exhaust temperature, and (ii) a second product of a second weighting factor and a second one of the sample flow rate, the emission concentration, the system operating duration, the exhaust pressure, and the exhaust temperature, the second weighting factor having a different value than the first weighting factor.

In one example, the method further includes determining the contamination index based on (i) a first result of a first one of the sample flow rate, the emission concentration, the system operating duration, the exhaust pressure, and the exhaust temperature raised to the power of a first exponent, and (ii) a second result of a second one of the sample flow rate, the emission concentration, the system operating duration, the exhaust pressure, and the exhaust temperature raised to the power of a second exponent, the second exponent having a different value than the first exponent.

In one example, the method further includes determining the contamination index at regular intervals to yield a plurality of contamination index values, and identifying potential contamination of at least one of the emissions test system and the emissions test system component when a sum of the contamination index values is greater than a predetermined value.

In one example, the method further includes recommending that a user perform maintenance on the emissions test system when the sum of the contamination index values is greater than the predetermined value, and setting the sum of the contamination index values to zero when the user indicates that the maintenance has been performed.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

Emissions test systems include various components that tend to become contaminated over time by particles in the exhaust gas under test. Such components include gaseous emissions analyzers, particle/particulate/smoke detectors, flow meters, sensors, pumps, valves, and filters. If any of these components become contaminated, the results of emissions tests conducted using the emissions test system may be inaccurate and/or the emissions test system may become inoperable.

Some controllers for emissions test systems monitor the operating duration of an emissions test system and recommend maintenance at predetermined intervals of system operation. For example, such controllers may recommend maintenance every 1000 hours of system operation regardless of the operating conditions of the emissions test system such as the concentration of emissions in exhaust gas under test or the flow rate of the exhaust gas. However, using components of an emissions test system in a "dirty" environment (e.g., higher emissions concentrations) will likely require earlier and/or more maintenance than using the components in a "clean" environment (e.g., lower emissions concentrations). Thus, performing maintenance on an emissions test system at predetermined intervals of system operation risks either contamination of system components or performing maintenance more than necessary.

Some controllers for emissions test systems recommend maintenance for a component of an emissions test system based on the performance of that component without taking into account the operating conditions of other components or areas of the system. For example, some controllers trigger an alarm when a pump is unable to achieve a commanded pressure, when a pressure differential across a filter is greater than a predetermined value, or when a signal output by a sensor or analyzer become saturated (e.g., a signal output by an emissions concentration sensor indicates 10 particles per million (ppm) when there are no emissions (0 ppm) in the exhaust gas under test). Such controllers take a reactive approach by recommending maintenance after components are contaminated rather than a preventative approach by recommending maintenance before components are contaminated. Taking a reactive approach to recommending maintenance may cause inaccuracies in the emissions test results and/or cause damage to the components of the emissions test system.

A system and method according to the present disclosure determines a contamination index based on the operating conditions of an emissions test system, and identifies potential contamination based on the contamination index. In one example, the system and method determines the contamination index at regular intervals (e.g., every second) to yield a plurality of contamination index values, and the system and method identifies potential contamination when a sum of the contamination index values is greater than a predetermined limit. When potential contamination is identified, the system and method may recommend that maintenance be performed on the emissions test system. In addition, the system and method may set the sum of the contamination index values to zero when the user indicates that the maintenance has been performed.

By taking into account system operating conditions, the system and method prevent contamination of system components without recommending that more maintenance be performed than necessary. In addition, the predetermined limit for the contamination index is set at a value to ensure that potential contamination is identified before system components are contaminated. Thus, the system and method take a preventative approach by recommending maintenance before components are contaminated rather than a reactive approach by recommending maintenance after components are contaminated. As a result, the system and method avoid inaccuracies in emissions test results and damage to system components.

Figure 1:
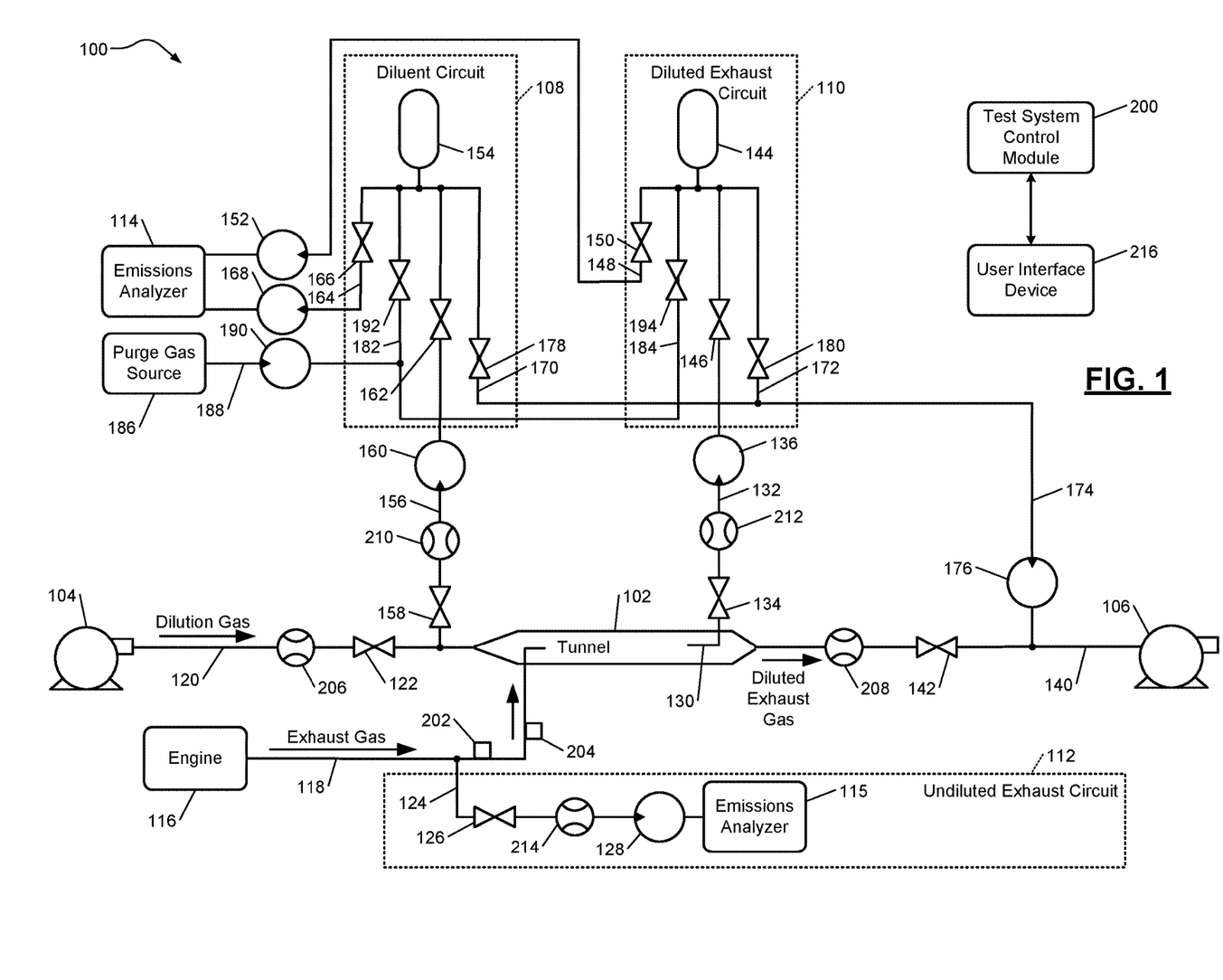
FIG. 1 is a functional block diagram of an example emissions test system according to the present disclosure.

Referring now to FIG. 1, an emissions test system 100 includes a dilution tunnel 102, an upstream blower 104, a downstream blower 106, a diluent circuit 108, a diluted exhaust circuit 110, an undiluted exhaust circuit 112, a first emissions analyzer 114, and a second emissions analyzer 115. The dilution tunnel 102 receives exhaust gas produced by an engine 116 through an exhaust gas supply line 118. The exhaust gas supply line 118 supplies the exhaust gas from the engine 116 to the dilution tunnel 102.

The dilution tunnel 102 also receives a dilution gas through a dilution gas supply line 120. The upstream blower 104 is disposed upstream of the dilution tunnel 102, and the upstream blower 104 sends the dilution gas through the dilution gas supply line 120 and to the dilution tunnel 102. The dilution gas may be ambient air, in which case the upstream blower 104 may draw the dilution gas from the surrounding environment. The upstream blower 104 may be a variable speed blower, and the speed of the upstream blower 104 may be adjusted to adjust the rate at which the dilution gas flows through the dilution tunnel 102. Additionally or alternatively, a valve 122 may be disposed in the dilution gas supply line 120, and the position of the valve 122 may be adjusted to adjust the flow rate of the dilution gas through the dilution tunnel 102.

The undiluted exhaust circuit 112 includes an undiluted exhaust supply line 124, an undiluted exhaust extraction valve 126, and/or an undiluted exhaust extraction pump 128. The emissions analyzer 115 may also be considered part of the undiluted exhaust circuit 112. The undiluted exhaust supply line 124 supplies a sample of exhaust gas from the exhaust gas supply line 118 to the emissions analyzer 115. The emissions analyzer 115 analyzes the undiluted exhaust gas sample to determine the concentrations of emissions contained therein. The emissions analyzer 115 may include a particle sampler, a microsoot sensor, and/or a smoke meter.

The undiluted exhaust extraction valve 126 may be disposed in the undiluted exhaust supply line 124, and the position of the undiluted exhaust extraction valve 126 may be adjusted to adjust the rate at which the undiluted exhaust gas sample is extracted through the undiluted exhaust supply line 124. Additionally or alternatively, the undiluted exhaust extraction pump 128 may be disposed in the undiluted exhaust supply line 124, and the speed of the undiluted exhaust extraction pump 128 may be adjusted to adjust the rate at which the diluted exhaust gas sample is extracted through the undiluted exhaust supply line 124. In one example, the undiluted exhaust extraction pump 128 is operated at a constant speed, and the position of the undiluted exhaust extraction valve 126 is adjusted to adjust the extraction rate of the diluted exhaust gas through the undiluted exhaust supply line 124.

The exhaust gas from the engine 116 is diluted with the dilution gas in the dilution tunnel 102. A diluted exhaust sample probe 130 extracts a sample of the diluted exhaust gas, and a diluted exhaust supply line 132 supplies the diluted exhaust gas sample from the diluted exhaust sample probe 130 to the diluted exhaust circuit 110. A diluted exhaust extraction valve 134 may be disposed in the diluted exhaust supply line 132, and the position of the diluted exhaust extraction valve 134 may be adjusted to adjust the rate at which the diluted exhaust gas sample is extracted through the diluted exhaust sample probe 130. Additionally or alternatively, a diluted exhaust extraction pump 136 may be disposed in the diluted exhaust supply line 132, and the speed of the diluted exhaust extraction pump 136 may be adjusted to adjust the rate at which the diluted exhaust gas sample is extracted through the diluted exhaust sample probe 130. In one example, the diluted exhaust extraction pump 136 is operated at a constant speed, and the position of the diluted exhaust extraction valve 134 is adjusted to adjust the extraction rate of the diluted exhaust gas through the diluted exhaust sample probe 130. The diluted exhaust sample probe 130, the diluted exhaust supply line 132, the diluted exhaust extraction valve 134, and the diluted exhaust extraction pump 136 may be considered part of the diluted exhaust circuit 110.

The portion of the diluted exhaust gas that is not extracted by the diluted exhaust sample probe 130 is expelled from the dilution tunnel 102 to the atmosphere through a dilution tunnel exhaust line 140. A valve 142 may be disposed in the dilution tunnel exhaust line 140, and the position of the valve 142 may be adjusted to adjust the rate at which the diluted exhaust gas flows through the dilution tunnel 102. Additionally or alternatively, the downstream blower 106 may be disposed downstream of the dilution tunnel 102, and the speed of the downstream blower 106 may be adjusted to adjust the rate at which the diluted exhaust gas flows through the dilution tunnel 102.

In various implementations, the emissions test system 100 may include only one of the upstream and downstream blowers 104 and 106. The upstream blower 104 and/or the downstream blower 106 may be controlled to force a constant volume of diluted exhaust gas through the dilution tunnel 102. In this regard, the emissions test system 100 may be a CVS system. However, the methods of the present disclosure for determining a contamination level of a system and/or device also apply to partial flow systems such as a bag mini dilutor.

The diluted exhaust circuit 110 includes a diluted exhaust sample collector 144 that collects the diluted exhaust gas sample extracted by the diluted exhaust sample probe 130. The diluted exhaust sample collector 144 may be a sample bag or a sample filter. A diluted exhaust fill valve 146 may be disposed in the diluted exhaust supply line 132, and the diluted exhaust fill valve 146 may be opened or closed to allow or prevent the flow of the diluted exhaust gas sample to the diluted exhaust sample collector 144. Although only one diluted exhaust sample collector 144 is shown, the system 100 may include a plurality of diluted exhaust sample collectors, and each diluted exhaust sample collector may collect a sample of diluted exhaust gas during one test phase of an emissions test schedule.

The emissions analyzer 114 analyzes the diluted exhaust gas sample collected by the diluted exhaust sample collector 144 to determine the concentrations of emissions contained therein. The emissions analyzer 114 may be a gaseous emissions analyzer that measures the concentrations of gaseous emissions such as carbon monoxide, carbon dioxide, nitrogen oxides, and hydrocarbon. The diluted exhaust gas sample is sent from the diluted exhaust sample collector 144 to the emissions analyzer 114 through a diluted exhaust read line 148. A diluted exhaust read valve 150 may be disposed in the diluted exhaust read line 148, and the diluted exhaust read valve 150 may be opened or closed to allow or prevent the flow of the diluted exhaust gas sample from the first clean diluted exhaust sample collector 144 to the emissions analyzer 114. Additionally or alternatively, a diluted exhaust read pump 152 may be disposed in the diluted exhaust read line 148, and the speed of the diluted exhaust read pump 152 may be adjusted to adjust the rate at which the diluted exhaust gas sample flows from the diluted exhaust sample collector 144 to the emissions analyzer 114.

The diluent circuit 108 includes a diluent sample collector 154 that collect a sample of the dilution gas flowing through the dilution gas supply line 120. A diluent sample supply line 156 supplies the dilution gas sample from the dilution gas supply line 120 to the diluent sample collector 154. A diluent extraction valve 158 may be disposed in the diluent sample supply line 156, and the position of the diluent extraction valve 158 may be adjusted to adjust the rate at which the dilution gas sample is extracted from the dilution gas supply line 120. Additionally or alternatively, a diluent extraction pump 160 may be disposed in the diluent sample supply line 156, and the speed of the diluent extraction pump 160 may be adjusted to adjust the rate at which the dilution gas sample is extracted from the dilution gas supply line 120. In one example, the diluent extraction pump 160 is operated at a constant speed, and the position of the diluent extraction valve 158 is adjusted to adjust the extraction rate of the dilution gas sample. The diluent sample supply line 156, the diluent extraction valve 158, and the diluent extraction pump 160 may be considered part of the diluent circuit 108.

The diluent sample collector 154 may be a sample bag or a sample filter. A diluent fill valve 162 may be disposed in the diluent sample supply line 156, and the diluent fill valve 162 may be opened or closed to allow or prevent the flow of the dilution gas sample to the diluent sample collector 154. Although only one diluent sample collector 154 is shown, the system 100 may include a plurality of diluent sample collectors, and each diluent sample collector may collect a sample of dilution gas during one test phase of an emissions test schedule.

The emissions analyzer 114 analyzes the dilution gas sample collected by the diluent sample collector 154 to determine the concentration of emissions contained therein. The emissions analyzer 114 may account for the concentration of emissions contained in the dilution gas sample when determining the concentration of emissions contained in the diluted exhaust gas sample. For example, if the mass of the dilution gas in the diluted exhaust gas sample is equal to the mass of the dilution gas in the dilution gas sample, the emissions analyzer 114 may subtract the concentration of emissions in the dilution gas sample from the concentration of emissions in the diluted exhaust gas sample to obtain the concentration of emissions in the exhaust gas contained in the diluted exhaust gas sample.

The diluted exhaust gas sample is sent from the diluent sample collector 154 to the emissions analyzer 114 through a diluent read line 164. A diluent read valve 166 may be disposed in the diluent read line 164, and the diluent read valve 166 may be opened or closed to allow or prevent the flow of the dilution gas sample from the diluent sample collector 154 to the emissions analyzer 114. Additionally or alternatively, a diluent read pump 168 may be disposed in the diluent read line 164, and the speed of the diluent read pump 168 may be adjusted to adjust the rate at which the dilution gas sample flows from the diluent sample collector 154 to the emissions analyzer 114.

The emissions test system 100 further includes a diluent vent line 170 and a diluted exhaust vent line 172 for venting gas samples from the diluent sample collector 154 and the diluted exhaust sample collector 144, respectively. In the example shown, the diluent vent line 170 and the diluted exhaust vent line 172 converge into a single vent line 174 that extends to the dilution tunnel exhaust line 140, and a vent pump 176 is disposed in the vent line 174 to draw gas samples through the vent line 174. In various implementations, the diluent vent line 170 and the diluted exhaust vent line 172 may not converge into a single vent line and/or may vent gas samples directly to the atmosphere. In addition, a vent pump (not shown) may be disposed in each of the vent lines 170, 172 in place of the vent pump 176.

A diluent vent valve 178 may be disposed in the diluent vent line 170, and the diluent vent valve 178 may be opened or closed to allow or prevent the flow of the dilution gas sample from the diluent sample collector 154 to the dilution tunnel exhaust line 140. Similarly, a diluted exhaust vent valve 180 may be disposed in the diluted exhaust vent line 172, and the diluted exhaust vent valve 180 may be opened or closed to allow or prevent the flow of the diluted exhaust gas sample from the diluted exhaust sample collector 144 to the dilution tunnel exhaust line 140.

The emissions test system 100 further includes a diluent purge line 182 and a diluted exhaust purge line 184 for proving purge gas to the diluent sample collector 154 and the diluted exhaust sample collector 144, respectively. The purge gas may be a clean gas, such as ambient air that has not been mixed with exhaust gas. The purge gas is provided by a purge gas source 186, which may simply be the atmosphere or may be a filter that filters ambient air to yield the purge gas. In the implementation shown, a single purge line 188 extends from the purge gas source 186 and splits into the diluent purge line 182 and the diluted exhaust purge line 184, and a purge pump 190 is disposed in the purge line 188 to send purge gas through the purge line 188. In various implementations, the diluent purge line 182 and the diluted exhaust purge line 184 may extend from the purge gas source 186 independent from one another, and a purge pump (not shown) may be disposed in each of the purge lines 182, 184.

A diluent purge valve 192 may be disposed in the diluent purge line 182, and the diluent purge valve 192 may be opened or closed to allow or prevent the flow of purge gas from the purge gas source 186 to the diluent sample collector 154. Similarly, a diluted exhaust purge valve 194 may be disposed in the diluted exhaust purge line 184, and the diluted exhaust purge valve 194 may be opened or closed to allow or prevent the flow of purge gas from the purge gas source 186 to the diluted exhaust sample collector 144.

The emissions test system 100 further includes a test system control module 200 that controls various actuators of the emissions test system 100 based on signals received from various sensors of the emissions test system 100. The actuators of the emissions test system 100 include the blowers 104, 106, the valves 122, 126, 134, 142, 146, 150, 158, 162, 166, 178, 180, 192, 194, and the pumps 128, 136, 152, 160, 168, 176, 190. The sensors of the emissions test system 100 include the emissions analyzers 114, 115, an exhaust temperature sensor 202, an exhaust pressure sensor 204, a dilution gas flow meter 206, a diluted exhaust flow meter 208, a diluent sample flow meter 210, a diluted sample flow meter 212, and an undiluted sample flow meter 214.

The diluent sample flow meter 210, the diluted sample flow meter 212, and the undiluted sample flow meter 214 may be considered part of the diluent circuit 108, the diluted exhaust circuit 110, and the undiluted exhaust circuit 112, respectively.

The test system control module 200 outputs various control signals to control the actuators of the emissions test system 100. The test system control module 200 outputs a blower control signal (FIG. 2) to each of the blowers 104, 106, and the blower control signal indicates a target duty cycle or target speed of the respective blower. The test system control module 200 outputs a valve control signal (FIG. 2) to each of the valves 122, 126, 134, 142, 146, 150, 158, 162, 166, 178, 180, 192, 194, and the valve control signal indicates a target position of the respective valve. The test system control module 200 outputs a pump control signal (FIG. 2) to each of the pumps 128, 136, 152, 160, 168, 176, 190, and the pump control signal indicates a target duty cycle or target speed of the respective pump.

The exhaust temperature sensor 202 measures the temperature of exhaust gas flowing through the exhaust gas supply line 118 and outputs an exhaust temperature signal (FIG. 2) indicating the exhaust temperature. The exhaust pressure sensor 204 measures the pressure of exhaust gas flowing through the exhaust gas supply line 118 and outputs an exhaust pressure signal (FIG. 2) indicating the exhaust pressure. The exhaust temperature and pressure sensors 202 and 204 output the exhaust temperature and pressure signals to the test system control module 200.

The dilution gas flow meter 206 measures the flow rate of dilution gas in the dilution gas supply line 120 and outputs a dilution gas flow rate signal (FIG. 2) indicating the dilution gas flow rate. The diluted exhaust flow meter 208 measures the flow rate of diluted exhaust gas in the dilution tunnel exhaust line 140 and outputs a diluted exhaust flow rate signal (FIG. 2) indicating the diluted exhaust flow rate. The diluent sample flow meter 210 measures the flow rate of the dilution gas sample flowing through the diluent sample supply line 156 and outputs a diluent sample flow rate signal (FIG. 2) indicating the diluent sample flow rate. The diluted sample flow meter 212 measures the flow rate of the diluted exhaust gas sample flowing through the diluted exhaust supply line 132 and outputs a diluted sample flow rate signal (FIG. 2) indicating the diluted sample flow rate. The undiluted sample flow meter 214 measures the flow rate of the undiluted exhaust gas sample flowing through the undiluted exhaust supply line 124 and outputs an undiluted sample flow rate signal (FIG. 2) indicating the undiluted sample flow rate. The dilution gas flow meter 206, the diluted exhaust flow meter 208, the diluent sample flow meter 210, the diluted sample flow meter 212, and the undiluted sample flow meter 214 output their respective flow rate signals to the test system control module 200.

The test system control module 200 determines a contamination index based on measurements made by the sensors, and identifies potential contamination of the emissions test system 100 and/or a component thereof based on the contamination index. The test system control module 200 may determine the contamination index at regular intervals to yield a plurality of contamination index values, and identify potential contamination when a sum of the contamination index values is greater than a predetermined value. In addition, when potential contamination is identified, the test system control module 200 may control a user interface device 216 to inform a user of the potential contamination and/or recommend that maintenance be performed on the system 100. Further, the test system control module 200 may control the user interface device 216 to prompt the user to indicate when the maintenance has been performed, and set the sum of the contamination index values to zero when the user does so.

The user interface device 216 may include an electronic display (e.g., a touchscreen) that is operable to display a visual message, such as text and/or images, and/or to generate electronic signals in response to user input (e.g., a user touching the touchscreen). In addition, the user interface device 216 may include a speaker that is operable to generate a sound or an audible message, and the user interface device 216 may include a microphone that is operable to receive verbal commands from the user. The test system control module 200 outputs a user interface device (UID) control signal (FIG. 2) to the user interface device 216, and the UID control signal indicates a visual and/or audible message to be communicated by the user interface device 216. The test system control module 200 may also receive a UID input signal (FIG. 2) from the user interface device 216, and the UID input signal may indicate a message from the user such as a message indicating that the recommended maintenance has been performed.

Figure 2:
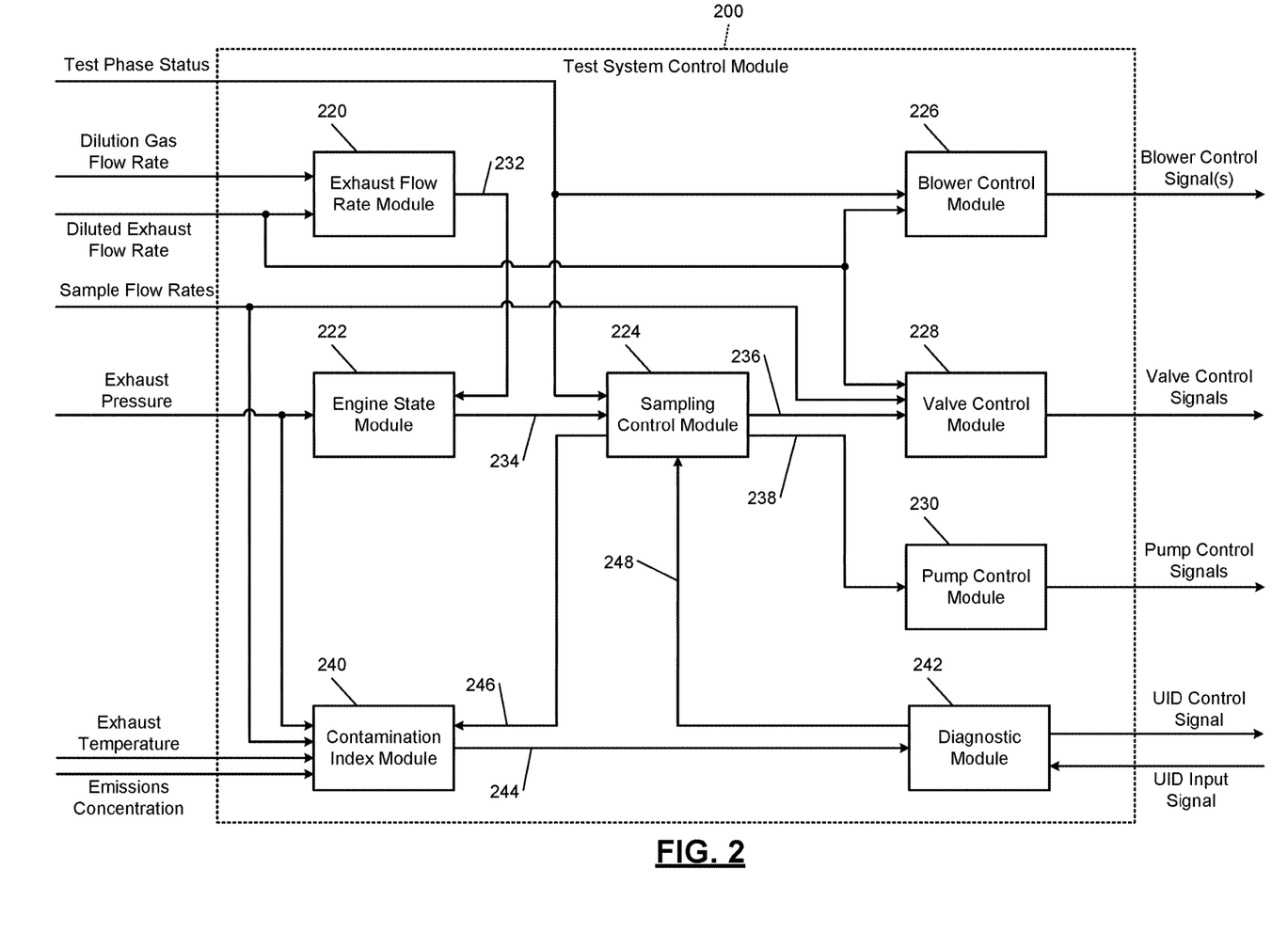
FIG. 2 is a functional block diagram of an example test system control module according to the present disclosure.

Referring now to FIG. 2, an example implementation of the test system control module 200 includes an exhaust flow rate module 220, an engine state module 222, a sampling control module 224, a blower control module 226, a valve control module 228, and a pump control module 230. The exhaust flow rate module 220 determines the flow rate of exhaust gas flowing through the exhaust gas supply line 118 and outputs a signal 232 indicating the same. In one example, the exhaust flow rate module 220 subtracts the dilution gas flow rate measured by the dilution gas flow meter 206 from the diluted exhaust flow rate measured by the diluted exhaust flow meter 208 to obtain the flow rate of exhaust gas flowing through the exhaust gas supply line 118.

In various implementations, the flow rate of exhaust gas flowing through the exhaust gas supply line 118 may be obtained from a powertrain control module (not shown) that controls the engine 116 and/or measured directly in the exhaust supply line 118. Alternatively, the exhaust flow rate module 220 may set the exhaust flow rate equal to a product of (i) the diluted exhaust flow rate measured by the diluted exhaust flow meter 208 and (ii) a ratio of a concentration of an emission (e.g., carbon dioxide) in the exhaust gas supply line 118 to a concentration of the same emission in the dilution tunnel exhaust line 140. Before determining this ratio, the exhaust flow rate module 220 may subtract the concentration of the emission in the dilution gas supply line 120 from the concentration of the emission in the dilution tunnel exhaust line 140. The emissions test system 100 may include one or more sensors (not shown) that measure the concentration of the emission in the dilution gas supply line 120 and/or the dilution tunnel exhaust line 140. Alternatively, the concentration of the emission in the dilution gas supply line 120 may be a predetermined (e.g., fixed) value.

The engine state module 222 determines whether the engine 116 is on (e.g., operating) or off (e.g., not operating) and outputs a signal 234 indicating the same. The engine state module 222 may determine whether the engine 116 is on or off based on an input from the powertrain control module. Additionally or alternatively, the engine state module 222 may determine whether the engine 116 is on or off based on the magnitudes and/or frequency of pulsations in the exhaust pressure signal that is output by the exhaust pressure sensor 204. In one example, the engine state module 222 determines that the engine 116 is on when the magnitude of a pulsation in the exhaust pressure signal is greater than a first value. In another example, the engine state module 222 determines that the engine 116 is on when the frequency of pulsations in the exhaust pressure signal is greater than a first frequency.

The first frequency may be predetermined based on the number of cylinders in the engine 116 and the idle speed of the engine 116. For example, the first frequency may be set to a value that is less than or equal to a product of the number of cylinders in the engine 116 and the idle speed of the engine 116. The first value may also be predetermined. For example, the first value may be set to an expected change in the pressure of exhaust gas produced by the engine 116 due to a combustion event in a cylinder of the engine 116.

The engine state module 222 may determine whether the engine 116 is on or off based on both the magnitudes and frequency of pulsations in the exhaust pressure signal output. For example, the engine state module 222 may identify pulsations in the exhaust pressure signal output that have a frequency greater than or equal to the first frequency (referred to herein as higher frequency pulsations), and determine the average value of the magnitudes of the pulsations identified. The engine state module 222 may then determine that the engine 116 is on when the average value of the magnitudes of the higher frequency pulsations is greater than or equal to the first value.

The blower control module 226 controls the upstream blower 104 to force diluted exhaust gas through the dilution tunnel 102 at the target flow rate. Additionally or alternatively, the blower control module 226 controls the downstream blower 106 to draw diluted exhaust gas through the dilution tunnel 102 at the target flow rate. The blower control module 226 controls the upstream blower 104 and/or the downstream blower 106 by outputting the blower control signal(s). As discussed above, the blower control signal(s) indicate a target duty cycle or target speed of the respective blower. The blower control module 226 may adjust the target duty cycle or target speed of the upstream blower 104 and/or the downstream blower 106 to minimize a difference between the diluted exhaust flow rate measured by the diluted exhaust flow meter 208 and the target flow rate.

The blower control module 226 may control the upstream blower 104 and/or the downstream blower 106 to maintain the diluted exhaust flow rate at the target flow rate for the entire duration of a test schedule. Thus, the blower control module 226 may activate the upstream blower 104 and/or the downstream blower 106 when the first test phase of the test schedule begins, and deactivate the upstream blower 104 and/or the downstream blower 106 when the last test phase of the test schedule ends. The blower control module 226 may receive a test phase status signal indicating when each test phase of the test schedule begins and ends and the order of the test phase (e.g., first, second, third, last), and therefore indicating when the test schedule begins and ends.

The valve control module 228 may adjust the position of the valve 122 to adjust the flow rate of the dilution gas through the dilution tunnel 102. Additionally or alternatively, the valve control module 228 may adjust the position of the valve 142 to adjust the rate at which the diluted exhaust gas flows through the dilution tunnel 102. The valve control module 228 may adjust the position of the valve 142 to maintain the diluted exhaust flow rate at the target flow rate for the entire duration of a test schedule. For example, the valve control module 228 may open the valve 142 when the first test phase of the test schedule begins, and close the valve 142 when the last test phase of the test schedule ends. The valve control module 228 may also receive the test phase status signal indicating when each test phase of the test schedule begins and ends and the order of each test phase.

The test phase status signal may be generated by a test schedule execution module (not shown) that executes the test schedule in response to a user input received via the user interface device 216 (e.g., a user pressing a button or touching an icon on a touchscreen). The test schedule execution module may be included in the test system control module or may be a separate module that communicates with the test system control module. The test schedule execution module may store a plurality of test schedules and select a test schedule to execute from the plurality of test schedules based on the user input. Each test schedule may include a predetermined number of test phases. Each test phase may have a predetermined duration and/or specify a target vehicle speed with respect to time.

The test phase status signal may indicate the target vehicle speed with respect to time in addition to indicating when each test phase starts and ends and the order of each test phase. The test schedule module may output the test phase status signal to the powertrain control module, which may control the engine 116 and/or an electric motor (not shown) to propel a vehicle (not shown) according to the test schedule. The test schedule module may also output the test phase status signal to a dynamometer control module (not shown), which may control a dynamometer (not shown) to adjust a load applied to the engine 116 and/or to wheels of the vehicle. For example, the test phase status signal may also indicate changes in road grade with respect to time, and the dynamometer control module may adjust the load applied to the engine 116 and/or the wheels to simulate those changes in road grade.

The sampling control module 224 coordinates operation of the valve control module 228 and the pump control module 230 to direct sample gas to the sample collectors 144, 154 during each test phase of the test schedule. In addition, the sampling control module 224 coordinates operation of the valve control module 228 and the pump control module 230 to send gas samples from the sample collectors 144, 146, to the emissions analyzer 114 after each test phase. Further, the sampling control module 224 coordinates operation of the valve control module 228 and the pump control module 230 to send purge gas to the sample collectors 144, 154 after gas samples are sent to the emissions analyzer 114. Moreover, the sampling control module 224 coordinates operation of the valve control module 228 and the pump control module 230 to vent gas samples from the sample collectors 144, 154. The sampling control module 224 may use the test phase status signal to determine when each test phase of the test schedule start and ends.

In the discussion below, the sampling control module 224 opens and closes the valves 126, 134, 146, 150, 158, 162, 166, 178, 180, 192, 194. The sampling control module 224 may accomplish this by outing a signal 236 to the valve control module 228 indicating a desired position (e.g., opened or closed) of each valve. Also, in the discussion below, the sampling control module 224 activates and deactivates the pumps 128, 136, 152, 160, 168, 176, 190. The sampling control module 224 may accomplish this by outing a signal 238 to the pump control module 230 indicating a desired state (e.g., activated or deactivated) of the each pump.

An emissions test schedule may include multiple test phases. For example, the U.S. Environmental Protection Agency (EPA) Federal Test Procedure includes a cold start phase, a cold stabilized phase, and a hot start phase. During each test phase, the sampling control module 224 opens the diluted exhaust extraction valve 134 and activates the diluted exhaust extraction pump 136 to extract a sample of diluted exhaust gas from the dilution tunnel 102. In addition, the sampling control module 224 opens the diluted exhaust fill valve 146 to send the diluted exhaust gas sample to the diluted exhaust sample collector 144. The emissions test system 100 may include a plurality of diluted exhaust sample collectors as discussed above, and the sampling control module 224 may direct a diluted exhaust sample to one of the sample collectors during each test phase.

Also, during each test phase, the sampling control module 224 opens the diluent extraction valve 158 and activates the diluent extraction pump 160 to extract a sample of dilution gas from the dilution gas supply line 120. In addition, the sampling control module 224 opens the diluent fill valve 146 to send the dilution gas sample to the diluent sample collector 154. The emissions test system 100 may include a plurality of diluent sample collectors as discussed above, and the sampling control module 224 may direct a dilution gas sample to one of the sample collectors during each test phase.

In various implementations, the sampling control module 224 may only direct diluted exhaust gas and dilution gas to the diluted exhaust sample collector 144 and the diluent sample collector 154, respectively, when the engine 116 is on during a test phase. However, the sampling control module 224 may direct dilution gas to the sample collectors 144, 154 regardless of whether the engine 116 is on or off at some point in time during the test phase to ensure that the sizes of the samples are sufficient for the emissions analyzer 114. The sample control module 274 may determine this point in time based on the amount of gas collected and the amount of time remaining in the test phase.

After samples are collected, the sample collectors 144, 154, the sampling control module 224 opens the read valves 150, 166 and activates the read pumps 152, 168 to direct the samples to the emissions analyzer 114. Next, the sampling control module 224 activates the purge pump 190 and opens the purge valves 192, 194 to send purge gas to the sample collectors 144, 154. Then, the sampling control module 224 activates the vent pump 176 and opens the vent valves 178, 180 to vent the purge gas from the sample collectors 144, 154.

The sampling control module 224 also opens the undiluted exhaust extraction valve 126 and activates the undiluted exhaust extraction pump 128 to extract samples of undiluted exhaust gas from the exhaust gas supply line 118 and to send the undiluted exhaust gas samples to the emissions analyzer 115. The sampling control module 224 may direct undiluted exhaust gas to the emissions analyzer 115 when the sampling control module 224 directs diluted exhaust gas to the diluted exhaust sample collector 144. Alternatively, the sampling control module 224 may direct undiluted exhaust gas and diluted exhaust gas to the emissions analyzer 115 and the diluted exhaust sample collector 144, respectively, at different times.

The example implementation of the test system control module 200 shown in FIG. 2 further includes a contamination index module 240 and a diagnostic module 242. The contamination index module 240 determines a contamination index based on at least one, two, or three (e.g., all) of the following parameters: the sample flow rate(s) from the flow meter(s) 210, 212, and/or 214; the emission concentration(s) from the emissions analyzer(s) 114 and/or 115; the operating duration of the emissions test system 100, the exhaust temperature from the exhaust temperature sensor 202; and the exhaust pressure from the exhaust pressure sensor 204. The contamination index module 240 outputs a signal 244 indicating the value of the contamination index.

The contamination index module 240 may determine the contamination index using a function (e.g., an equation) or mapping (e.g., a lookup table) that relates one, two, or three or more of the aforementioned parameters to the contamination index. The contamination index module 240 may determine a single contamination index for the entire emissions test system 100. Alternatively, the contamination index module 240 may determine a contamination index for each component of the emissions test system 100 that may be contaminated. Components of the emissions test system 100 that may be contaminated include the blowers 104, 106, the valves 122, 126, 134, 142, 146, 150, 158, 162, 166, 178, 180, 192, 194, the pumps 128, 136, 152, 160, 168, 176, 190, the sample collectors 144, 154, the emissions analyzers 114, 115, the sensors 202, 204, and the flow meters 208, 210, 212, 214.

In one example, the contamination index module 240 determines the contamination index using a relationship such as $$CI = W_1 \dot{V}^{e1} + W_2 \Phi^{e2} + W_3 t^{e3} + W_4 T^{e4} + W_5 P^{e5}, \quad (1)$$

where CI is the contamination index, $\dot{V}$ is the sample flow rate from the diluent sample flow meter 210, the diluted sample flow meter 212, or the undiluted sample flow meter 214, $\Phi$ is the emission concentration from the emissions analyzer 114 or 115, t is the operating duration of the emissions test system 100, T is the exhaust temperature from the exhaust temperature sensor 202, and P is the exhaust pressure from the exhaust pressure sensor 204.

$W_1$ is a first weighting factor applied to the sample flow rate, $W_2$ is a second weighting factor applied to the emission concentration, $W_3$ is a third weighting factor applied to the system operating duration, $W_4$ is a fourth weighting factor applied to the exhaust temperature, and $W_5$ is a fifth weighting factor applied to the exhaust pressure. The values of the weighting factors $W_1$, $W_2$, $W_3$, $W_4$, $W_5$ may be different than one another. Alternatively, two or more of the weighting factors $W_1$, $W_2$, $W_3$, $W_4$, $W_5$ may have the same value.

$e_1$ is a first exponent applied to the sample flow rate, $e_2$ is a second exponent applied to the emission concentration, $e_3$ is a third exponent applied to the system operating duration, $e_4$ is a fourth exponent applied to the exhaust temperature, and $e_5$ is a fifth exponent applied to the exhaust pressure. The values of the exponents $e_1$, $e_2$, $e_3$, $e_4$, and $e_5$ may be different than one another. Alternatively, two or more of the exponents $e_1$, $e_2$, $e_3$, $e_4$, $e_5$ may have the same value. In either case, the exponents $e_1$, $e_2$, $e_3$, $e_4$, $e_5$ may be higher order exponents (e.g., may be greater than or equal to 2).

The weighting factors $W_1$, $W_2$, $W_3$, $W_4$, $W_5$ and the exponents $e_1$, $e_2$, $e_3$, $e_4$, $e_5$ may be adjusted to increase or decrease the affect that the corresponding parameter has on the contamination index. For example, the first weighting value $W_1$ and/or the first exponent $e_1$ may be increased to increase the affect that the sample flow rate has on the contamination index and vice versa. In addition, the weighting factors $W_1$, $W_2$, $W_3$, $W_4$, $W_5$ and the exponents $e_1$, $e_2$, $e_3$, $e_4$, $e_5$ may be adjusted relative to one another to reflect the effect that the corresponding parameter has on the contamination level of the emissions test system 100 or a component thereof. For example, if the sample flow rate and the emissions concentration have a greater effect on the contamination level than the system operating duration, the exhaust pressure, and the exhaust temperature, the first weighting value $W_1$ and the second weighting value $W_2$ may be set to values that are greater than the third, fourth, and fifth weighting values $W_3$, $W_4$, and $W_5$.

If the contamination index module 240 determines a contamination index for each component of the emissions test system 100 that may be contaminated, the weighting factors $W_1$, $W_2$, $W_3$, $W_4$, $W_5$ and the exponents $e_1$, $e_2$, $e_3$, $e_4$, $e_5$ may be selected based on the particular component that the contamination index is being determined for. For example, if the flow rate of the diluted exhaust gas sample 212 has a greater effect on the contamination level of the emissions analyzer 114 than that of the valve 142, the first weighting factor $W_1$ and the first exponent $e_1$ may be set to greater values when determining the contamination index for the emissions analyzer 114 than when determining the contamination index for the valve 142.

In another example, the contamination index module 240 may determine the contamination index using a relationship such as $$CI = \frac{(W_1 x_1^{e_1})(W_2 x_2^{e_2})}{W_3 x_3^{e_3}}, \qquad (2)$$

where $x_1$, $x_2$, and $x_3$ are respectively a first one, a second one, and a third one of the following parameters: the sample flow rate from the flow meter 210, 212, or 214; the emission concentration from the emissions analyzer 114 or 115; the operating duration of the emissions test system 100; the exhaust temperature from the exhaust temperature sensor 202; and the exhaust pressure from the exhaust pressure sensor 204. The sample flow rate in relationships (1) and (2) may be the instantaneous sample flow rate or the sample flow rate integrated with respect to time. The emissions concentration in relationships (1) and (2) may be a voltage, current, or mass indicated by the signal from the flow meter 210 or 212 and representative of the emissions concentration.

The sampling control module 224 may include a timer to track the system operating duration. The sampling control module 224 may increment the timer when the sampling control module 224 directs diluent to the diluent circuit 108, when the sampling control module 224 directs diluted exhaust gas to the diluted exhaust circuit 110, and/or when sampling control module 224 directs undiluted exhaust gas to the undiluted exhaust circuit 114. The sampling control module 224 may output a signal 246 indicating the system operating duration.

The diagnostic module 242 identifies potential contamination of the emissions test system 100 and/or a component thereof based on the contamination index. In one example, the contamination index module 240 determines the contamination index at regular intervals (e.g., every second) to yield a plurality of contamination index values, and the diagnostic module 242 identifies potential contamination when a sum of the contamination index values is greater than a predetermined value. In addition, when potential contamination is identified, the diagnostic module 242 may control the user interface device 216 to inform a user of the potential contamination and/or recommend that maintenance be performed on the emissions test system 100. Further, the diagnostic module 242 may control the user interface device 216 to prompt the user to indicate when the maintenance has been performed, and the diagnostic module 242 may set the sum of the contamination index values to zero when the user does so.

The predetermined value may be determined through experimentation using, for example, trial-and-error and/or a design of experiments. For example, the contamination index module 240 may determine the contamination index at regular intervals of system operation using relationship (1) or (2), and determine a sum of the contamination index values. Meanwhile, the emissions test system 100 may be visually inspected and/or the performance of components of the system 100 may be evaluated at regular intervals. When the visual inspection and/or performance evaluation indicates that a component of the emissions test system 100 is contaminated, the diagnostic module 242 may set the predetermined value equal to the sum of the contamination index values at that time.

The diagnostic module 242 may determine the predetermined value in the manner described above for different engine operating conditions (e.g., engine load, exhaust temperature), different test phases, different engine types, and/or for exhaust extracted upstream or downstream of an after treatment device. The diagnostic module 242 may use design of experiments to select engine operating condition(s), test phase(s), engine type(s), and/or exhaust extraction point(s) for which to determine the predetermined value. The diagnostic module 242 may set the predetermined value equal to the average value of all of the predetermined values determined.

If the contamination index is determined on a component basis, the predetermined value may also be determined on a component basis. For example, the contamination index module 240 may determine the contamination index for a component of the emissions test system 100 at regular intervals of system operation using relationship (1) or (2), and determine a sum of the contamination index values. Meanwhile, the component may be visually inspected and/or the performance of the component may be evaluated at regular intervals. When the visual inspection and/or performance evaluation indicates that the component is contaminated, the diagnostic module 242 may set the predetermined value equal to the sum of the contamination index values at that time.

Once the predetermined value is set, the contamination index module 240 may adjust one or more of the weighting factors $W_1$, $W_2$, $W_3$, $W_4$, $W_5$ and/or one or more of the exponents $e_1$, $e_2$, $e_3$, $e_4$, $e_5$ when a components fails a performance evaluation before sum of the contamination index values reaches the predetermined value. For example, if the emissions analyzer 114 fails a performance evaluation before the sum of the contamination index values reaches the predetermined value, the weighting factors and/or the exponents for the sample flow rate and the emissions concentration may be increased since those parameters have a large effect on the contamination level of the emissions analyzer 114. In turn, the contamination index module 240 may identify potential contamination in the emissions analyzer 114 before it fails a performance evaluation, which ensures that the analysis results of the analyzer 114 are accurate.

The diagnostic module 242 may recommend that maintenance be performed on a particular component of the emissions test system 100 when potential contamination is identified. For example, the diagnostic module 242 may recommend replacing a filter, replacing a sensor, and/or performing a new calibration on a sensor. The diagnostic module 242 may recommend maintenance on a particular component of the emissions test system 100 when the sum of the contamination index values determined for that component is greater than the predetermined value.

In addition, the diagnostic module 242 may output a signal 248 indicating when potential contamination is identified, and the sampling control module 224 may stop executing a test schedule when potential contamination is identified. For example, when potential contamination is identified, the sampling control module 224 may stop directing diluted exhaust gas to the diluted exhaust sample collector 144, stop directing dilution gas to the diluent sample collector 154, and/or stop directing undiluted exhaust gas to the emissions analyzer 115. In addition, the signal 248 may indicate when the recommended maintenance has been performed, and the sampling control module 224 may resume executing the test schedule when the maintenance has been performed.

Figure 3:
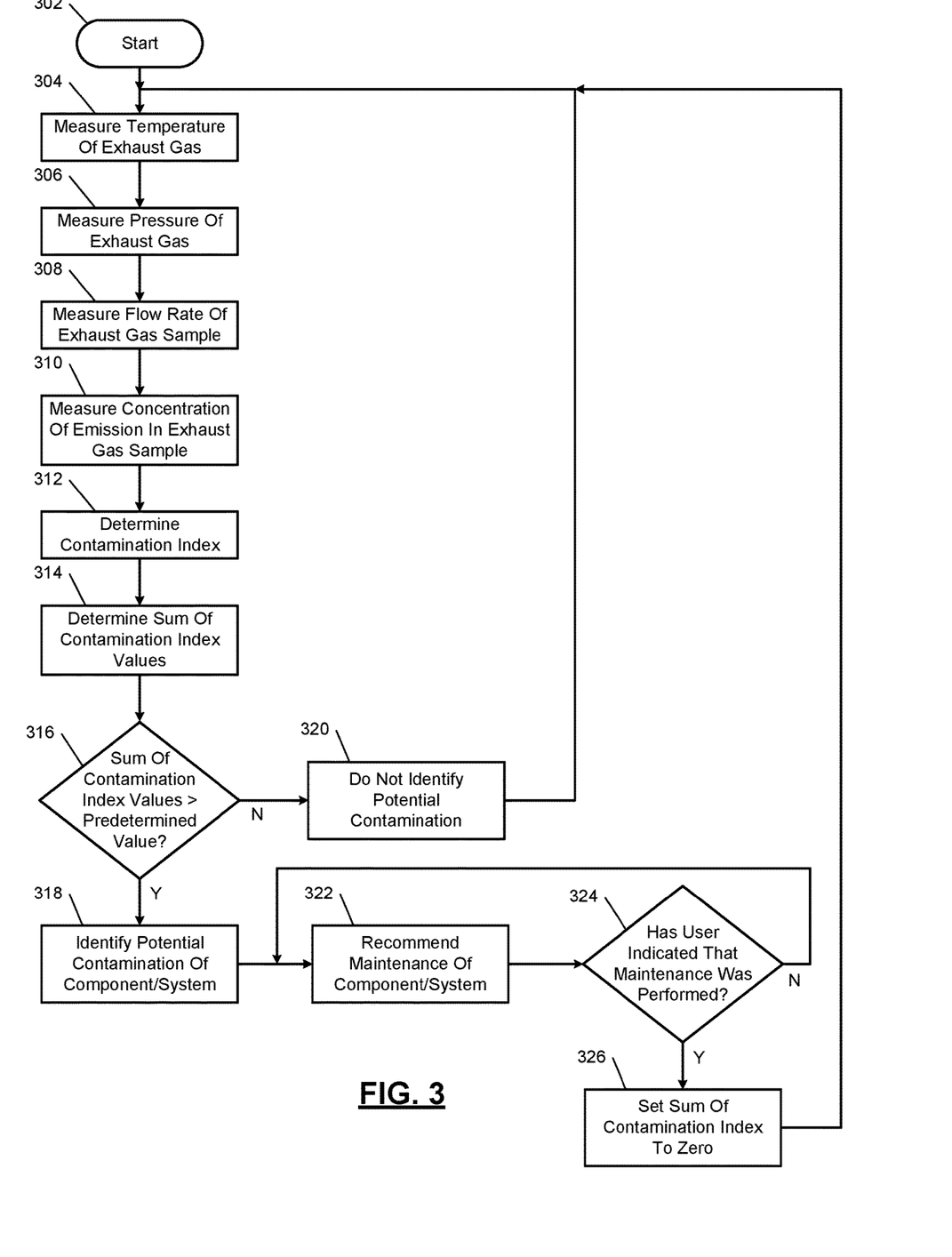
FIG. 3 is a flowchart illustrating example method for determining a contamination level of an emissions test system and/or a component thereof.

Referring now to FIG. 3, a method for determining a contamination level of the emissions test system 100 and/or a component thereof begins at 302. The method of FIG. 3 is described in the context of the modules of FIG. 2. However, the particular modules that perform the steps of the method of FIG. 3 may be different than those mentioned below and/or the method of FIG. 3 may be implemented apart from the modules of FIG. 2.

At 304, the exhaust temperature sensor 202 measures the temperature of exhaust gas flowing through exhaust gas supply line 118. At 306, the exhaust pressure sensor 204 measures the pressure of exhaust gas flowing through the exhaust gas supply line 118. At 308, the diluted sample flow meter 212 measures the flow rate of a diluted exhaust gas sample flowing through the diluted exhaust supply line 132. Additionally or alternatively, the diluent sample flow meter 210 may measure the flow rate of a dilution gas sample flowing through the diluent sample supply line 156. Additionally or alternatively, the undiluted sample flow meter 214 may measure the flow rate of an undiluted exhaust gas sample flowing through the undiluted exhaust supply line 124.

At 310, the emissions analyzer 114 determines the concentration(s) of one or more emissions in the diluted exhaust gas sample. Additionally or alternatively, the emissions analyzer 114 may determine the concentration(s) of one or more emissions in the dilution gas sample. Additionally or alternatively, the emissions analyzer 115 may determine the concentration(s) of one or more emissions in the undiluted exhaust gas sample.

At 312, the contamination index module 240 determines the contamination index at regular intervals of system operation to yield a plurality of contamination index values. At 314, the contamination index module 240 determines a sum of the contamination index values. At 316, the diagnostic module 242 determines whether the sum of the contamination index values is greater than the predetermined value. If the sum of the contamination index values is greater than the predetermined value, the method continues at 318, where the diagnostic module 242 identifies potential contamination of the emissions test system 100 and/or a component thereof. Otherwise, the method continues at 320, where the diagnostic module 242 does not identify potential contamination of the emissions test system 100 and/or a component thereof.

After 318, method continues at 322, where the diagnostic module 242 recommends that maintenance be performed on the emissions test system 100 and/or a component thereof. At 324, the diagnostic module 242 determines whether a user has indicated that the maintenance has been performed. If a user has indicated that the maintenance has been performed, the method continues at 326, where the contamination index module 240 sets the sum of the contamination index values to zero. Otherwise, the diagnostic module 242 continues to recommend that maintenance be performed. After 326, the method returns to 304 (i.e., the method restarts).

Figure 4:
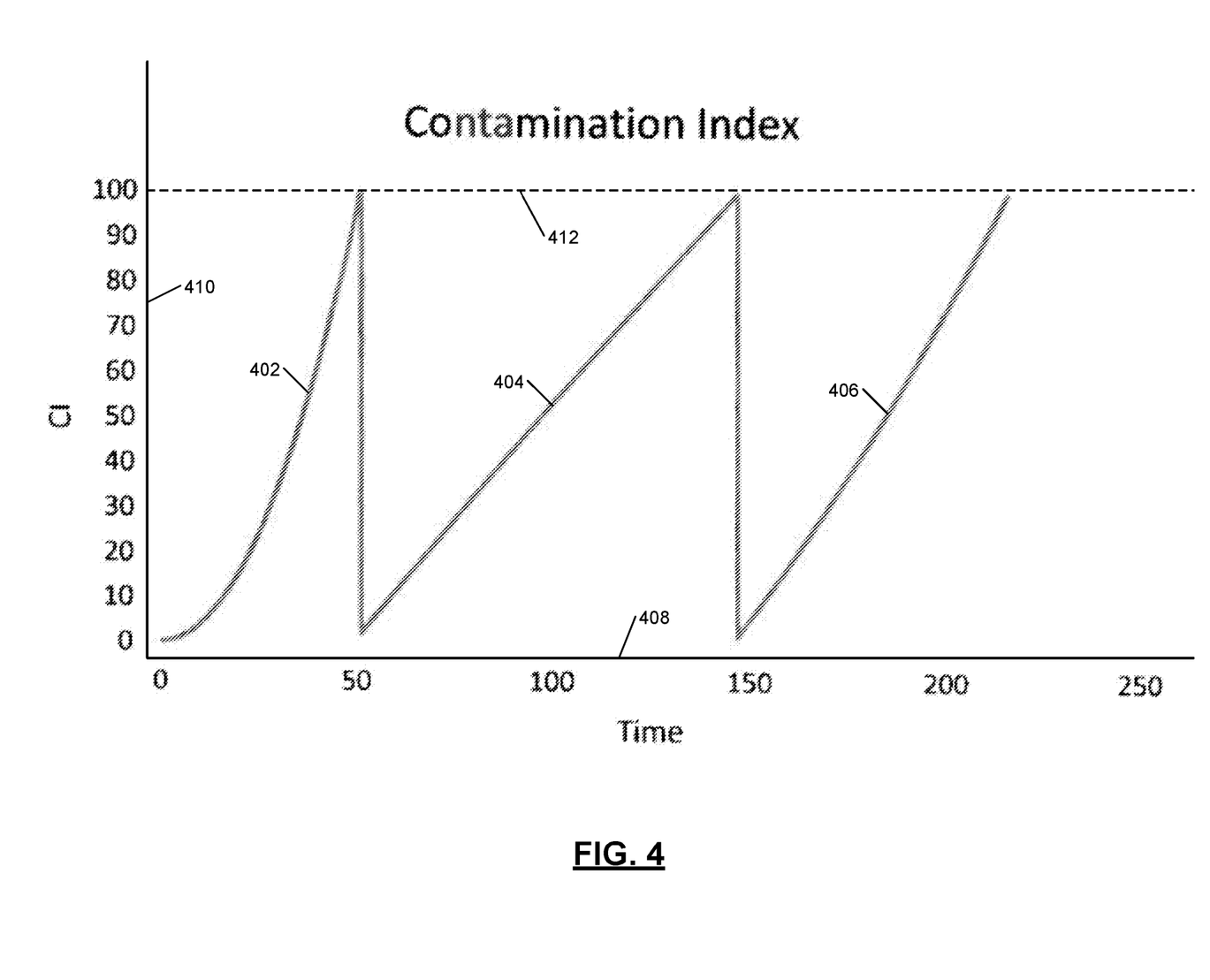
FIG. 4 is a graph illustrating ways in which a contamination level may increase with respect to time according to the present disclosure.

Referring now to FIG. 4, a first curve 402, a second curve 404, and a third curve 406 are plotted with respect to an x-axis 408 representing time in hours and a y-axis 410 representing the contamination index. The first, second, and third curves 402, 404, and 406 represent different ways in which the contamination index may increase respect to time. As used herein when referring to FIG. 4, the "contamination index" is the sum of the contamination index values. For example, during each iteration, the contamination index module 240 may determine new value of the contamination index using relationship (1) or (2), and set the contamination index equal to the sum of the new contamination index and the contamination index from the last iteration.

The contamination index indicated by each of the first, second, and third curves 402, 404, and 406 increases until the contamination index is equal to a predetermined value or limit 412. At that point, the contamination index module 240 sets the contamination index to zero. The limit 412 is equal to 100, as the contamination index has been normalized with respect to the limit 412. In other words, the contamination index is expressed as a percentage of the limit 412.

As indicated by the first curve 402, the contamination index may increase in an exponential manner with respect to time. Alternatively, as indicated by the second and third curves 404 and 406, the contamination index may increase in a linear manner with respect to time. In addition, as indicated by first, second, and third curves 402, 404, and 406, the contamination index may increase at different rates. To this end, the contamination index indicated by the first curve 402 increases from 0 to 100 over a period of 50 hours, the contamination index indicated by the second curve 404 increases from 0 to 100 over a period of 100 hours, and the contamination index indicated by the third curve 406 increases from 0 to 100 over a period of 75 hours. As indicated above, the rate at which the contamination index increase may depend on factors such as the sample flow rate, the emissions concentration, the exhaust temperature, and the exhaust pressure.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. An emissions test system comprising:
   at least one emissions test system component;
   an emissions analyzer configured to determine a concentration of an emission in a sample of exhaust gas from an engine;
   a contamination index module configured to determine a contamination index for the at least one emission test system component based on at least two of:
   a flow rate of the exhaust gas sample weighted by at least one of a first weighting factor and a first exponent associated with the emission test system component;
   the concentration of the emission in the exhaust gas sample weighted by at least one of a second weighting factor and a second exponent associated with the emission test system component;

an operating duration of the emissions test system weighted by at least one of a third weighting factor and a third exponent associated with the emission test system component;
a pressure of the exhaust gas weighted by at least one of a fourth weighting factor and a fourth exponent associated with the emission test system component; or
a temperature of the exhaust gas weighted by at least one of a fifth weighting factor and a fifth exponent associated with the emission test system component; and
a diagnostic module configured to identify potential contamination of the at least one emissions test system component based on the contamination index.

2. The emissions test system of claim 1 further comprising:
a dilution tunnel configured to receive the exhaust gas from the engine and dilution gas from a dilution gas source; and
a sample collector configured to receive a sample of diluted exhaust gas from the dilution tunnel, wherein the emissions analyzer is configured to determine the concentration of the emission in the diluted exhaust gas sample.

3. The emissions test system of claim 1 wherein the exhaust gas sample is undiluted.

4. The emissions test system of claim 1 wherein the contamination index module is configured to determine the contamination index based on the weighted flow rate and the weighted emission concentration.

5. The emissions test system of claim 1 wherein the contamination index module is configured to determine the contamination index based on at least three of the weighted flow rate, the weighted emission concentration, the weighted system operating duration, the weighted exhaust pressure, and the weighted exhaust temperature.

6. The emissions test system of claim 1 wherein the contamination index module is configured to determine the contamination index based on the weighted flow rate, the weighted emission concentration, the weighted system operating duration, the weighted exhaust pressure, and the weighted exhaust temperature.

7. The emissions test system of claim 1 wherein the contamination index module is configured to determine the contamination index based on:
a first product of one of the weighting factors and the corresponding one of the flow rate, the emission concentration, the system operating duration, the exhaust pressure, and the exhaust temperature; and
a second product of a second one of the weighting factors and the corresponding one of the sample flow rate, the emission concentration, the system operating duration, the exhaust pressure, and the exhaust temperature, the respective second one of the weighting factors having a different value than the first one of the weighting factors.

8. The emissions test system of claim 1 wherein the contamination index module is configured to determine the contamination index based on:
a first result of a first one of the sample flow rate, the emission concentration, the system operating duration, the exhaust pressure, and the exhaust temperature raised to the power of a respective first one of the exponents; and
a second result of a second one of the sample flow rate, the emission concentration, the system operating duration, the exhaust pressure, and the exhaust temperature raised to the power of a respective second one of the exponents, the respective second one of the exponents having a different value than the respective first one of the exponents.

9. The emissions test system of claim 1 wherein the contamination index module is configured to:
determine the contamination index at regular intervals to yield a plurality of contamination index values; and
identify potential contamination of the emissions test system component when a sum of the contamination index values is greater than a predetermined value associated with the emissions test system component.

10. The emissions test system of claim 9 wherein the contamination index module is configured to:
recommend that a user perform maintenance on the emissions test system component when the sum of the contamination index values is greater than the predetermined value; and
set the sum of the contamination index values to zero when the user indicates that the maintenance has been performed.

11. A method comprising:
determining a contamination index for a component of an emissions test system based on at least two of:
a flow rate of the exhaust gas sample weighted by at least one of a first weighting factor and a first exponent associated with the emission test system component;
the concentration of the emission in the exhaust gas sample weighted by at least one of a second weighting factor and a second exponent associated with the emission test system component;
an operating duration of the emissions test system weighted by at least one of a third weighting factor and a third exponent associated with the emission test system component;
a pressure of the exhaust gas weighted by at least one of a fourth weighting factor and a fourth exponent associated with the emission test system component; or
a temperature of the exhaust gas weighted by at least one of a fifth weighting factor and a fifth exponent associated with the emission test system component; and
identifying potential contamination of the at least one of the emissions test system component based on the contamination index.

12. The method of claim 11 wherein the exhaust gas sample is diluted with a dilution gas.

13. The method of claim 11 wherein the exhaust gas sample is undiluted.

14. The method of claim 11 further comprising determining the contamination index based on the weighted flow rate and the weighted emission concentration.

15. The method of claim 11 further comprising determining the contamination index based on at least three of the weighted flow rate, the weighted emission concentration, the weighted system operating duration, the weighted exhaust pressure, and the weighted exhaust temperature.

16. The method of claim 11 further comprising determining the contamination index based on the weighted flow rate, the weighted emission concentration, the weighted system operating duration, the weighted exhaust pressure, and the weighted exhaust temperature.

17. The method of claim 11 further comprising determining the contamination index based on:

a first product of one of the weighting factors and the corresponding one of the flow rate, the emission concentration, the system operating duration, the exhaust pressure, and the exhaust temperature; and a second product of a second one of the weighting factors and the corresponding one of the sample flow rate, the emission concentration, the system operating duration, the exhaust pressure, and the exhaust temperature, the second weighting factor having a different value than the first weighting factor.

18. The method of claim 11 further comprising determining the contamination index based on:

a first result of a first one of the sample flow rate, the emission concentration, the system operating duration, the exhaust pressure, and the exhaust temperature raised to the power of a respective first one of the exponents; and a second result of a second one of the sample flow rate, the emission concentration, the system operating duration, the exhaust pressure, and the exhaust temperature raised to the power of a respective second one of the exponents, the respective second one of the exponents having a different value than the respective first one of the exponents.

19. The method of claim 11 further comprising:

determining the contamination index at regular intervals to yield a plurality of contamination index values; and identifying potential contamination of the emissions test system component when a sum of the contamination index values is greater than a predetermined value associated with the emissions test system component.

20. The method of claim 19 further comprising:

recommending that a user perform maintenance on the emissions test system component when the sum of the contamination index values is greater than the predetermined value; and setting the sum of the contamination index values to zero when the user indicates that the maintenance has been performed.

* * * * *